(12) United States Patent
Julian et al.

(10) Patent No.: US 6,979,300 B1
(45) Date of Patent: Dec. 27, 2005

(54) MASSAGE SYSTEM (76) Inventors: Mark C. Julian, 8605 Woodcrest Dr., Port Richey, FL (US) 34668; Michael K. Julian, 8199 U.S. 19 North, Pinellas Park, FL (US) 33782

( * ) Notice: Subject to any disclaimer, the term of this patent is extended or adjusted under 35 U.S.C. 154(b) by 417 days.

(21) Appl. No.: 10/319,330

(22) Filed: Dec. 13, 2002

Related U.S. Application Data (60) Provisional application No. 60/340,598, filed on Dec. 14, 2001.

(51) Int. Cl.[7] ............................................. A61H 23/02
(52) U.S. Cl. ..................... 601/15; 601/22; 601/28; 601/70; 601/72; 601/50
(58) Field of Search .................... 601/15, 22, 50, 601/70, 72, 73, 27–32

(56) References Cited

U.S. PATENT DOCUMENTS

| | | | | |
|---|---|---|---|---|
| 2,276,510 | A | * | 3/1942 | Newton ..................... 601/62 |
| D384,160 | S | * | 9/1997 | Kusnets et al. ............. D24/215 |
| 5,725,483 | A | * | 3/1998 | Podolsky ..................... 601/15 |
| 5,797,859 | A | * | 8/1998 | Prehodka .................... 601/22 |
| 5,827,205 | A | * | 10/1998 | Iwamoto ..................... 601/78 |
| 6,210,349 | B1 | * | 4/2001 | Naruse et al. .............. 601/127 |
| 6,405,390 | B2 | * | 6/2002 | Kuen ........................... 4/622 |

* cited by examiner

Primary Examiner—Danton DeMille
(74) Attorney, Agent, or Firm—Ted Masters

(57) ABSTRACT

A massage system includes a magnetic massage head which produces a pulsating magnetic field. The massage system also includes a foot pad which includes raised areas for massaging the arch and toes of the user.

8 Claims, 11 Drawing Sheets

Fig_3

Fig_4

MASSAGE SYSTEM

CROSS REFERENCE TO RELATED APPLICATION

This application claims the filing benefit under 35 U.S.C. §119(e) of U.S. Provisional Application No. 60/340,598, filed Dec. 14, 2001, which is included herein by reference.

TECHNICAL FIELD

The present invention pertains generally to body massage, and more particularly to a portable massage system which can be utilized to massage virtually any part of the human body. The massage system includes a foot massage pad and an attachment having a magnetic massage head.

BACKGROUND OF THE INVENTION

Massage is a well know therapy for aching muscles. In ancient times, as well as the present, the art of massage is best performed by skilled experts who are knowledgeable in techniques of relieving muscle pain. Alternatively, massage systems and machines have been developed which emulate the actions of a masseuse, and which may be used in the privacy of one's home. The present invention discloses an improved massage system which enjoys several advantages over previous devices.

SUMMARY OF THE INVENTION

The present invention is directed to an improved massage system. As opposed to prior systems which only performed a few massaging functions, the present invention incorporates additional functions which greatly enhance usability and effectiveness. The present portable massage system gives a complete and versatile massage that can be performed by a user alone or with the assistance of another person. The present invention allows the user to perform massage on virtually any part of the body.

Dual controls on the system allow a person to turn the system ON or OFF and control the speed of a massage-producing motor without having to bend, stoop or move the machine. Magnets that spin around inside a magnetic head attachment, which is screwed into a vibrating unit, create a moving magnetic field which provides superior therapeutic results. A soft massage pad attachment provides the ability to give a better deeper therapeutic massage without the pain of hard sharper attachments. A specifically designed footpad gives the system the capability to provide therapeutic massage for the feet and also foot reflexology treatment.

In accordance with a preferred embodiment of the invention, a massage system includes a vibrating unit which has receptacles to receive various massage devices. One such massage device is a magnetic massage head which includes a rotating member which rotates about an axle when the vibrating unit is activated. A magnet is carried by the rotating member, so that when the vibrating unit is activated, the magnet rotates about the axle thereby creating a rotating magnetic field.

In accordance with another aspect of the invention, the rotating member includes a disc which is fabricated from a non-magnetic material, and the magnet is disposed within a sector of the disc, so that as the disc rotates about the axle the rotating magnetic field pulsates.

In accordance with another preferred embodiment of the invention, a foot pad is attachable to the vibrating unit, so that when the vibrating unit is activated, the foot pad vibrates. The foot pad has a front surface which has a plurality of foot-massaging knobs. The plurality of foot-massaging knobs includes a group of base knobs. The plurality of foot-massaging knobs also includes a group of raised first knobs, wherein the first knobs are taller than the base knobs. The group of first knobs is used to massage the arch of a user's foot.

In accordance with another aspect of the invention, the foot pad also contains two raised groups of second knobs which may be used to massage the toes of the user.

Other aspects of the present invention will become apparent from the following detailed description, taken in conjunction with the accompanying drawings, which illustrate, by way of example, the principles of the invention.

DETAILED DESCRIPTION OF THE INVENTION

Figure 1:
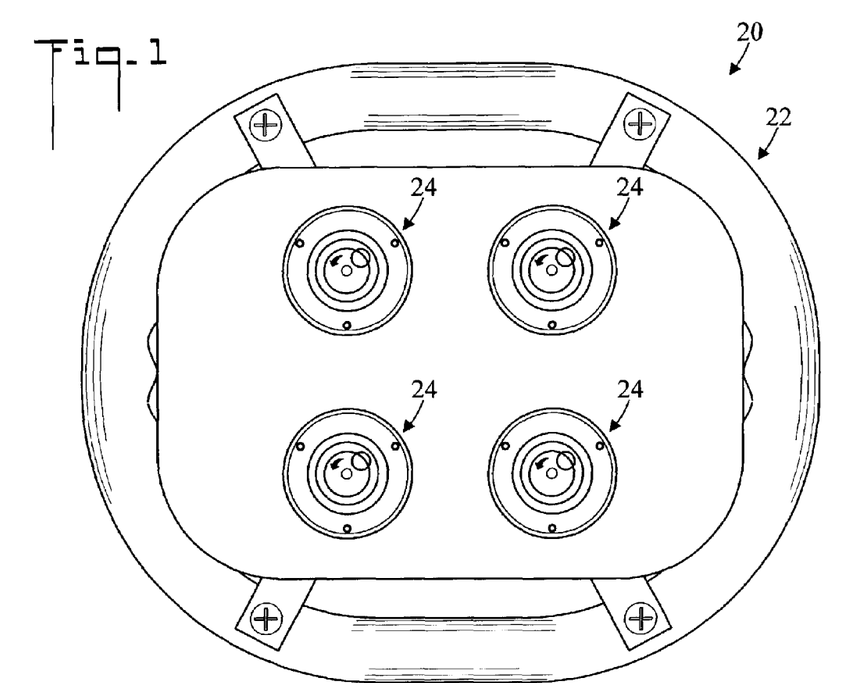
FIG. 1 is a top plan view of a massage system in accordance with the present invention.
Figure 2:
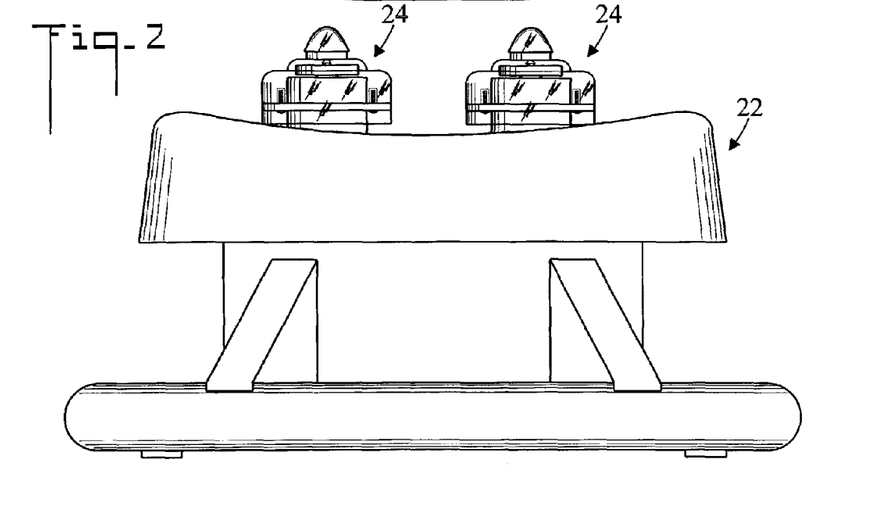
FIG. 2 is side elevation view of the massage system.
Figure 3:
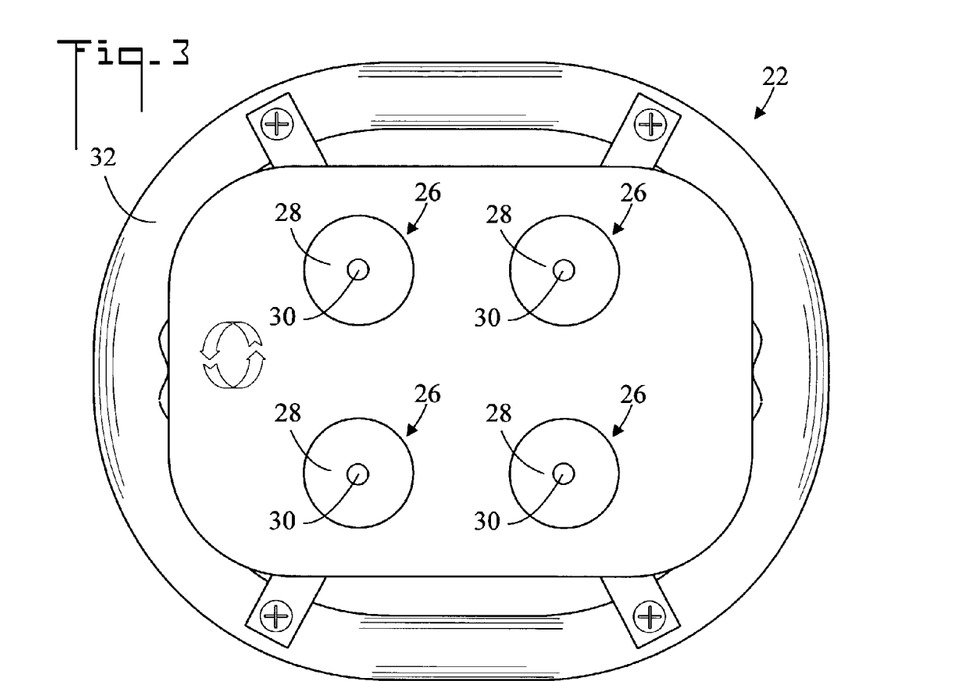
FIG. 3 is a top plan view of a vibrating unit.
Figure 4:
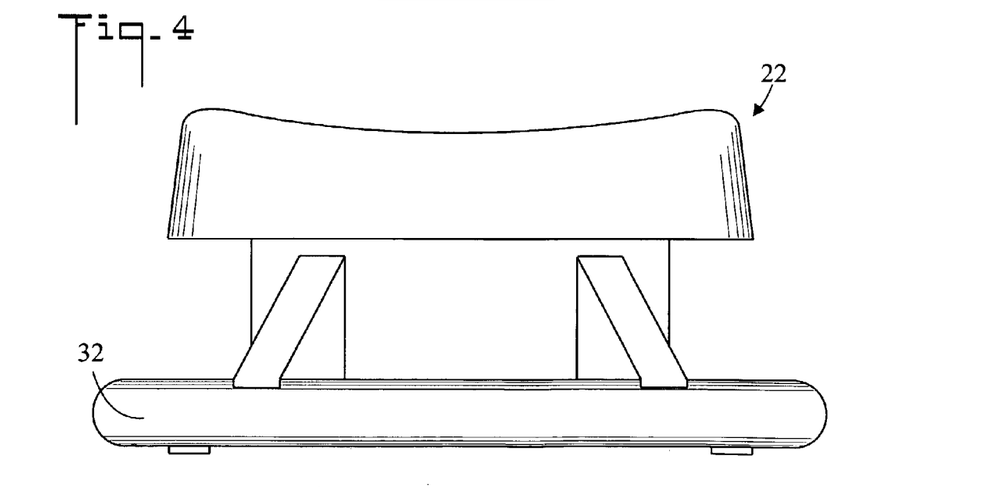
FIG. 4 is a side elevation view of the vibrating unit.
Figure 5:
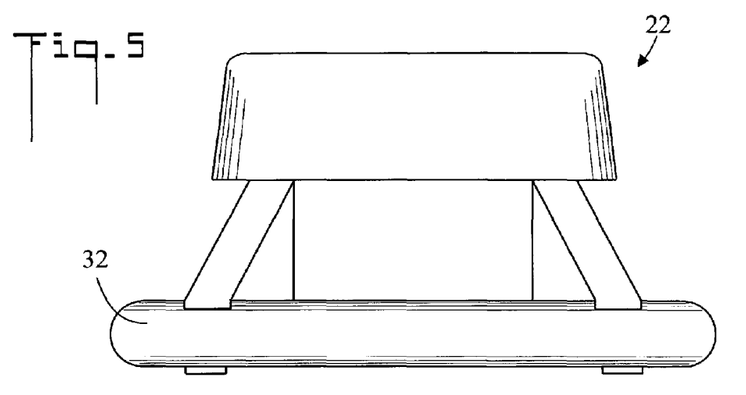
FIG. 5 is an end elevation view of the vibrating unit.
Figure 6:
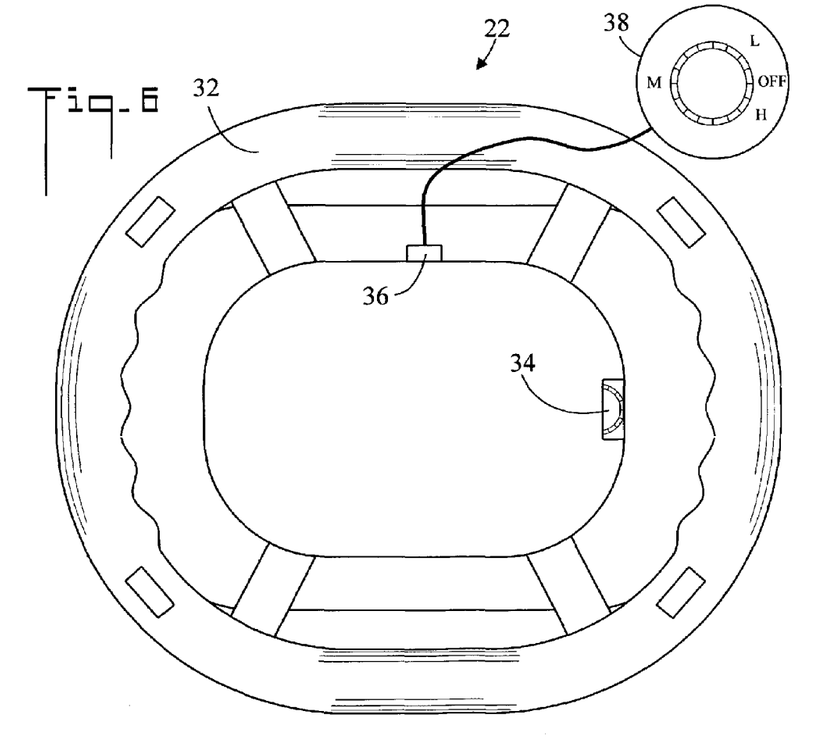
FIG. 6 is a bottom plan view of the vibrating unit.

Referring initially to FIGS. 1–2, there are illustrated top plan, and side elevation views respectively of a massage system in accordance with the present invention, generally designated as 20. Massage system 20 includes a vibrating unit 22 and a magnetic massage head 24.

Now referring to FIGS. 3–6, there are illustrated top plan, side elevation, end elevation, and bottom plan views respectively of vibrating unit 22. When vibrating unit 22 is activated, a motor causes vibrating unit 22 to vibrate in a rotary manner. Motor speeds of between 700 rpm and 3300 rpm have been found useful in the present invention. Vibrating unit 22 has at least one attachment-accepting receptacle 26. In the shown embodiment, vibrating unit 22 includes four spaced-apart attachment-accepting receptacles 26, each of which includes a recessed cavity 28 having a threaded female insert 30. Vibrating unit 22 further includes a handle 32 having a flattened steering wheel shape. Handle 32 is covered with a cushioning material such as rubber which absorbs some of the vibrational energy which would otherwise be passed along to the hands of a user. This permits the user to comfortably use vibrating unit 22 for longer periods of time. The cushioning material also provides the user with a superior gripping surface. Additionally, handle 32 serves as the supporting base of vibrating unit 22 in certain applications.

Vibrating unit 22 also includes an activation switch 34 which is used to turn vibrating unit 22 ON and OFF, and to control the intensity of vibrations by controlling the speed of the unit's motor. Vibrating unit 22 may also be controlled remotely. A remote control telephone-type jack 36 connects to a remote control unit 38, which allows ON, OFF, and vibration intensity control of vibrating unit 22. It may be appreciated that the remote control feature could also be implemented with wireless technology similar to a TV remote control.

Figure 7:
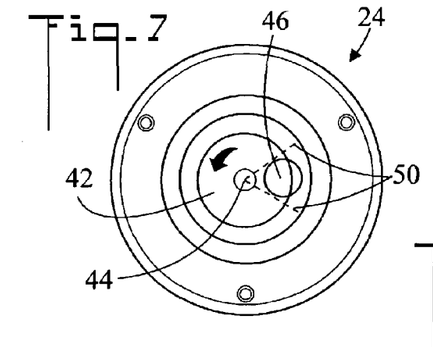
FIG. 7 is an enlarged top plan view of a magnetic massage head.
Figure 8:
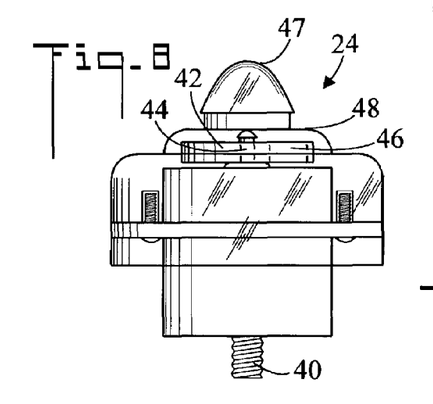
FIG. 8 is an enlarged side elevation view of the magnetic massage head.

Now referring to FIGS. 7–8, there are illustrated enlarged top plan and side elevation views respectively of magnetic massage head 24. A magnetic massage head 24 is removably attachable to receptacle 26 of vibrating unit 22 (refer to FIGS. 1 and 2). The attachment is effected via threaded insert 30 in vibrating unit 22 and a screw 40 on magnetic massage head 24. Magnetic massage head 24 includes a rotating member 42 (also refer to FIG. 9) which rotates about an axle 44 when vibrating unit 22 is activated (turned ON). A magnet 46 is carried by rotating member 42, so that when vibrating unit 22 is activated, magnet rotates 46 about axle 44 thereby creating a rotating magnetic field. In one possible embodiment, the entire rotating member 42 comprises magnet 46. However, in a preferred embodiment of the invention, rotating member disc 42 includes a disc which is fabricated from a non-magnetic material, and magnet 46 is only disposed within a sector 50 of the disc, so that as the disc rotates about axle 44 the rotating magnetic field pulsates. That is, a point near magnetic massage head 24 will experience rapidly alternating periods of magnetic field and no magnetic field. The pulsating magnetic field allows for a deeper more penetrating magnetic massage.

In an embodiment of the invention, magnet 46 has a strength of about 2000 gauss. In another embodiment of the invention, magnetic massage head 24 has a transparent housing 48 so that the rotation of rotating member 42 (disc) about axle 44 may be observed by the user. Magnetic massage head 24 further has a dome portion 47.

Figure 9:
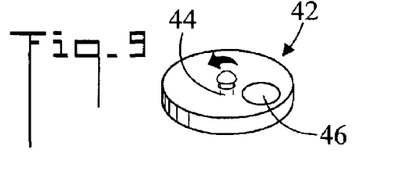
FIG. 9 is an enlarged perspective view of a rotating member.

FIG. 9 is an enlarged perspective view of a rotating member 42.

Figure 10:
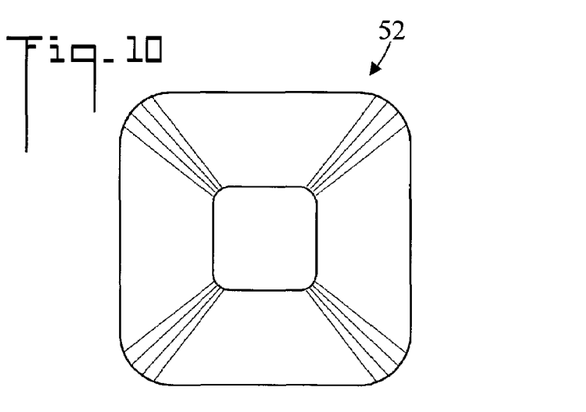
FIG. 10 is an enlarged top plan view of a massage pad.
Figure 11:
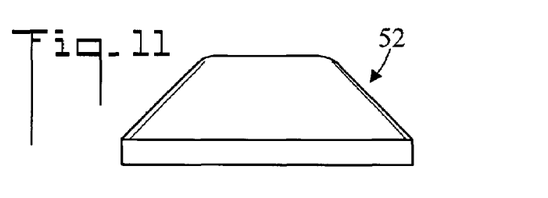
FIG. 11 is an enlarged side elevation view of the massage pad.
Figure 12:
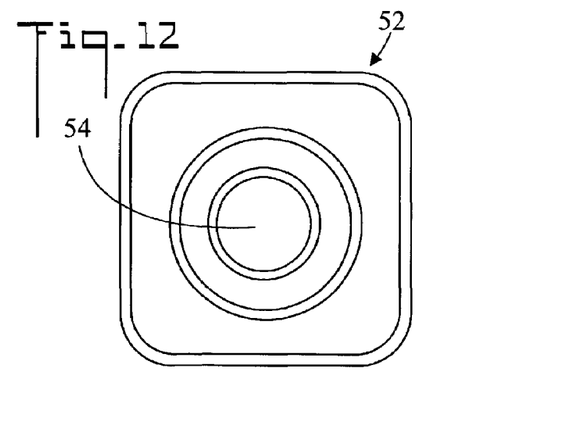
FIG. 12 is an enlarged bottom plan view of the massage pad.

FIGS. 10–12 are enlarged top plan, side elevation, and bottom plan views respectively of a massage pad 52. Massage pad 52 is shaped and dimensioned to removably attach to magnetic massage head 24. Massage pad 52 is fabricated from a flexible material, such as rubber or a polymer, and has a socket 54 which snuggly fits over dome 47 of magnetic massage head 24 (refer also to FIG. 13). Massage pad 52 has the shape of a truncated pyramid. Massage pad 52 is specifically designed with a flat top. The flat top, about 0.75 inches square, allows for a deep and penetrating massage without being obtrusive or damaging. With this design the massage is both deep and soft while covering more surface area.

Figure 13:
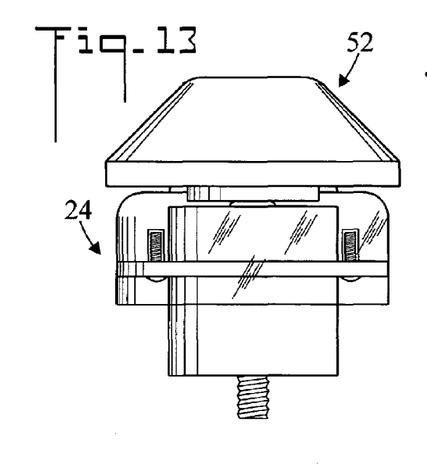
FIG. 13 is an enlarged side elevation view of the massage pad attached to the magnetic massage head.

FIG. 13 is an enlarged side elevation view of massage pad 52 attached to the magnetic massage head 24.

Figure 14:
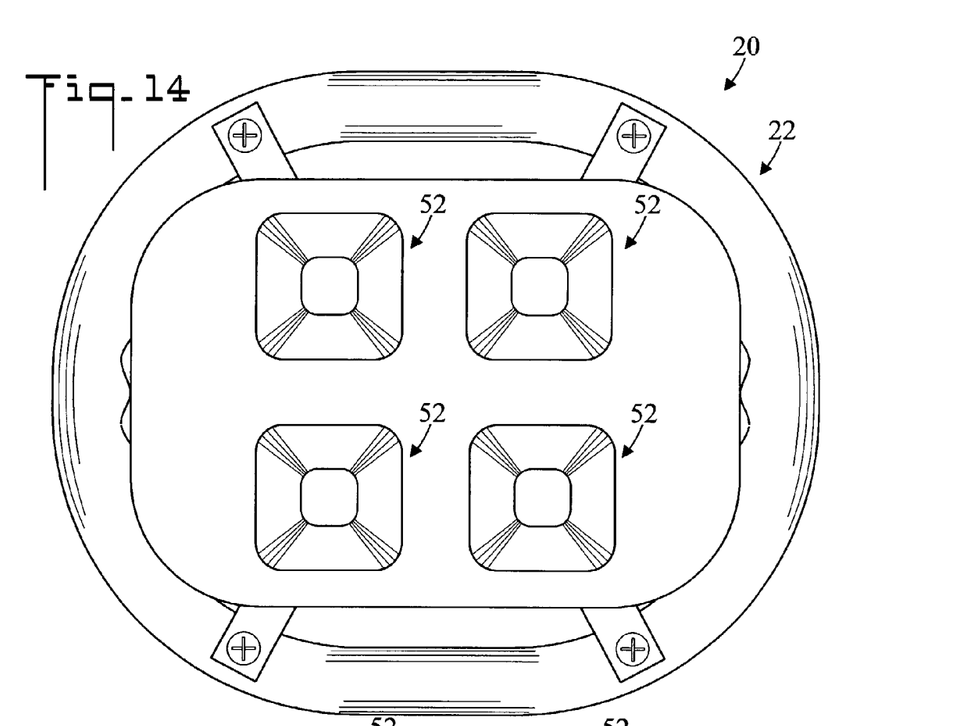
FIG. 14 is a top plan view of a second embodiment of the massage system.
Figure 15:
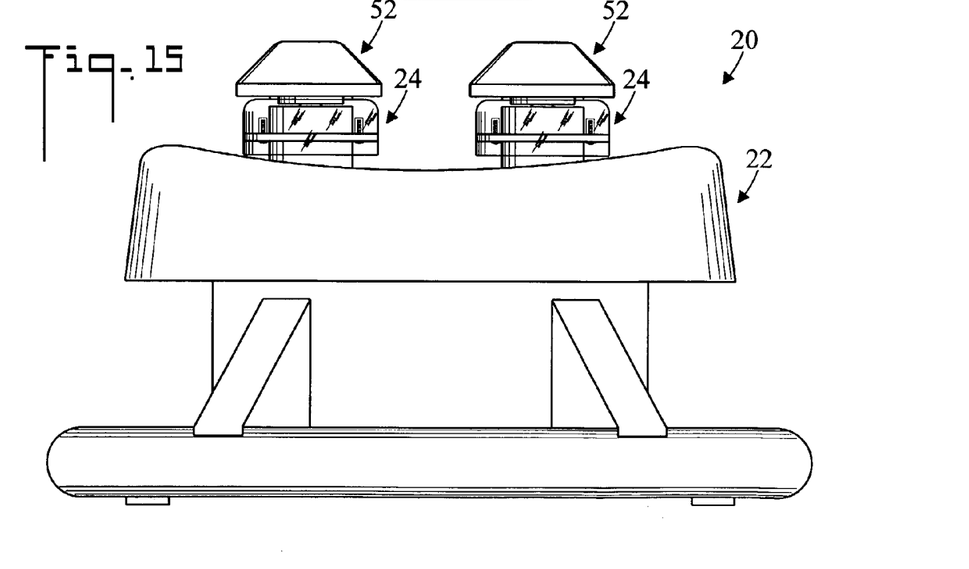
FIG. 15 is a side elevation view of the second embodiment of the massage system.

FIGS. 14–15 are top plan and side elevation views respectively of massage system 20 with magnetic massage head 24 installed in vibrating unit 22, and massage pad 52 attached to magnetic massage head 24.

Figure 16:
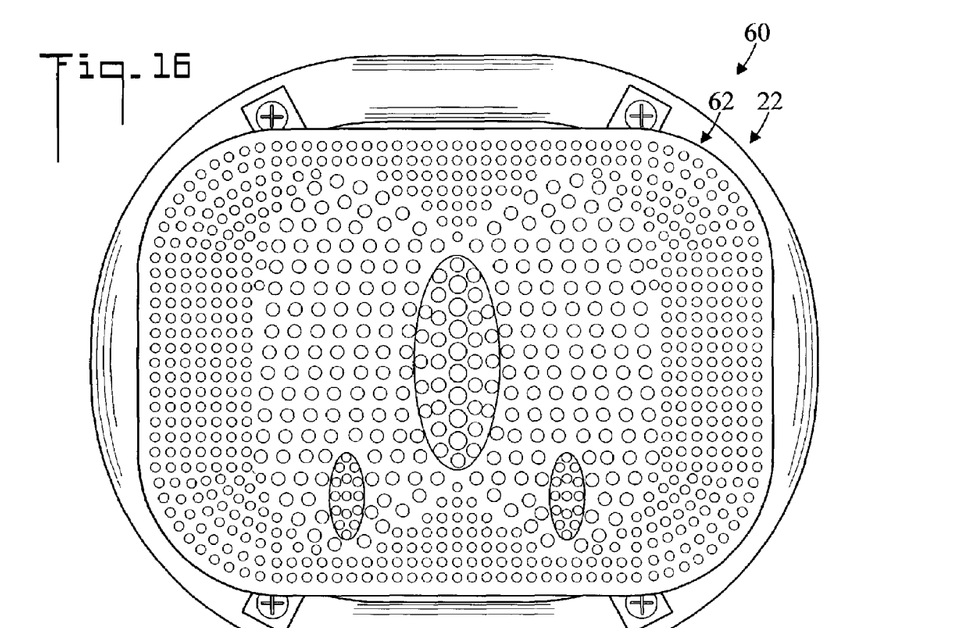
FIG. 16 is a top plan view of a second embodiment of the massage system.
Figure 17:
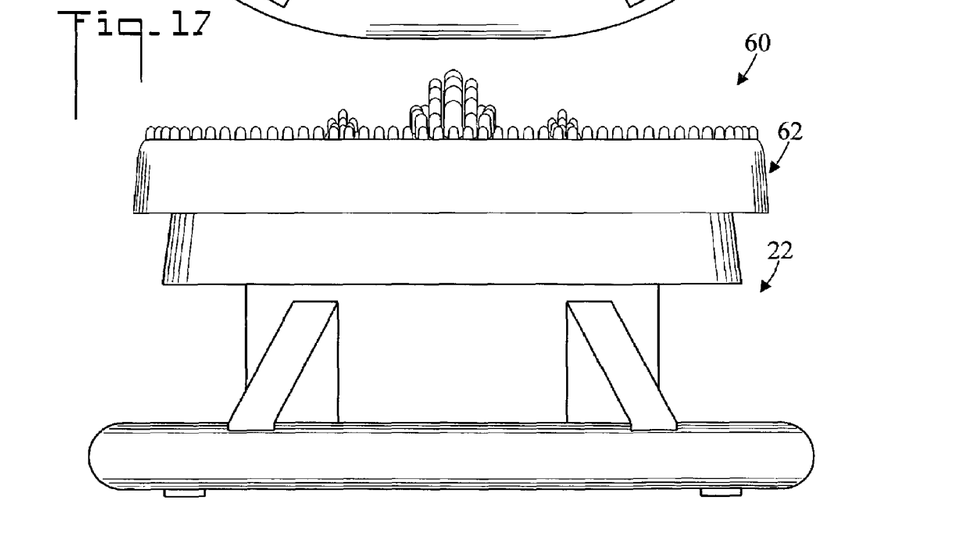
FIG. 17 is a side elevation view of the second embodiment.

Referring now to FIGS. 16–17, there are illustrated top plan and side elevation views respectively of a second embodiment of the massage system of the present invention, generally designated as 60. As with embodiment 20, massage system 60 includes vibrating unit 22 which has at least one attachment-accepting receptacle 24 (refer to FIGS. 3–6). A foot pad 62 is removably attachable to vibrating unit 22, so that when vibrating unit 22 is activated, foot pad 62 vibrates.

Now referring to FIGS. 18–21, there are illustrated top plan, side elevation, end elevation, and bottom plan views respectively of foot pad 62. Foot pad 62 is fabricated from a material such as rubber or a polymer which is flexible and yet has enough rigidity to impart vibrations into the foot of the user. Foot pad 62 includes a front surface 63 having a plurality of foot-massaging knobs, including knobs of at least two different widths (refer also to FIG. 22). The plurality of foot-massaging knobs includes a group of base knobs 64 having a maximum height H (above front surface 63). In an embodiment of the invention, all base knobs 64 are of substantially the same height H. The plurality of foot-massaging knobs also includes a group of raised first knobs 66 having a maximum height H1 which is greater than maximum height H of base knobs 64. First knobs 66 are useful in massaging the arch of the user's foot (refer also to FIG. 30). The plurality of foot-massaging knobs also includes a group of raised second knobs 68 having a maximum height H2 which is greater than maximum height H of base knobs 64, but less than maximum height H2 of first knobs 66. Second knobs 68 are useful in massaging the toes of the user's foot (refer also to FIG. 29). In the shown embodiment, two groups of second knobs 68 are provided so that a user may massage the toes of both feet simultaneously.

Figure 21:
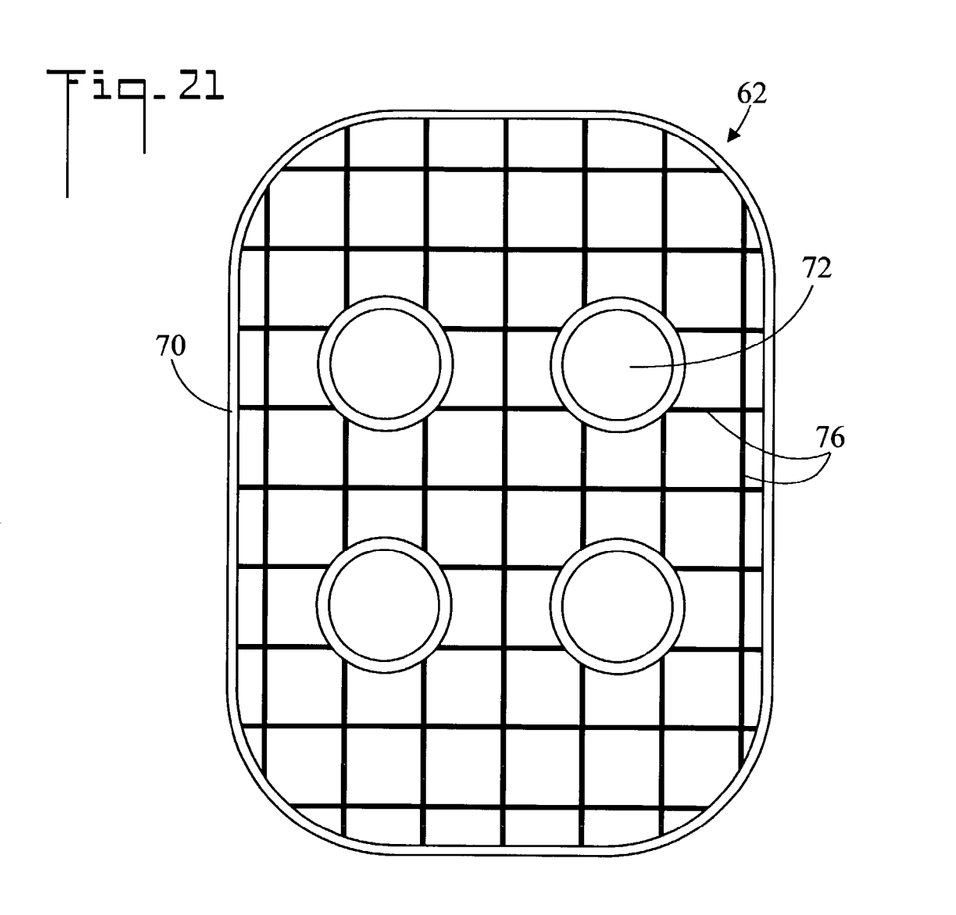
FIG. 21 is a bottom plan view of the foot pad.

Referring specifically to FIG. 21, foot pad 62 has a back side 70 opposite from front surface 62. Back side 70 includes at least one cavity 72. In the shown embodiment, four cavities 72 are provided. In the shown embodiment, back side 70 includes a grid of support walls 76 which serve to support front surface 62.

Figure 18:
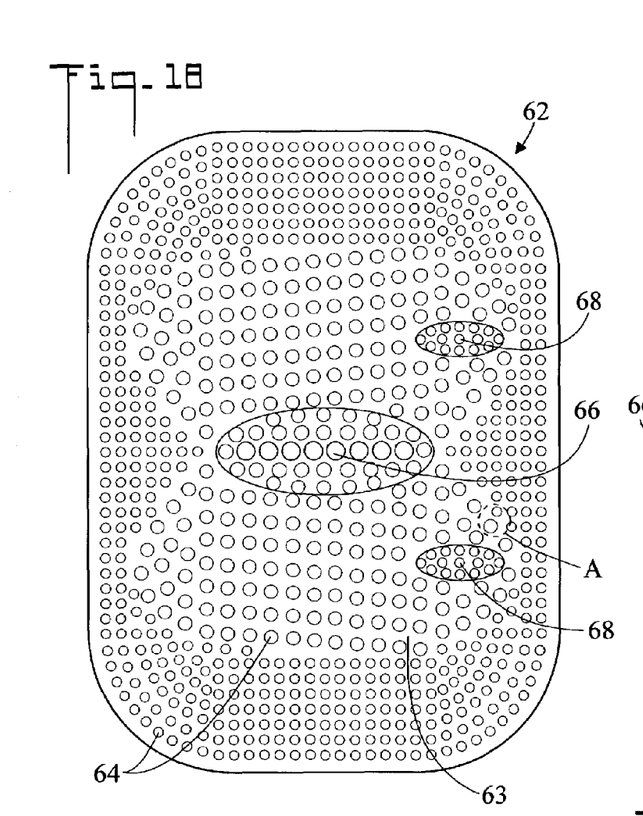
FIG. 18 is top plan view of a foot pad.
Figure 19:
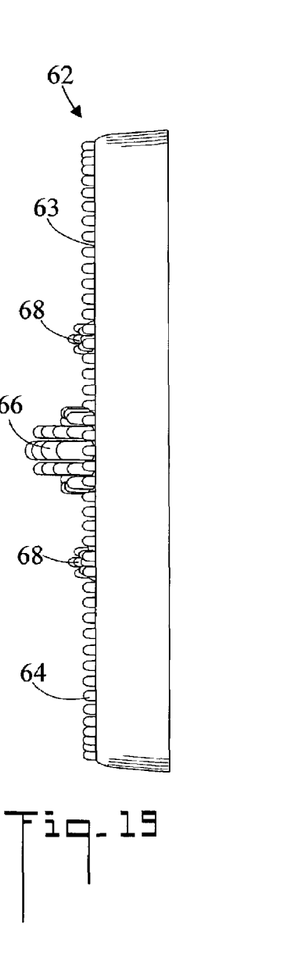
FIG. 19 is a side elevation view of the foot pad.
Figure 20:
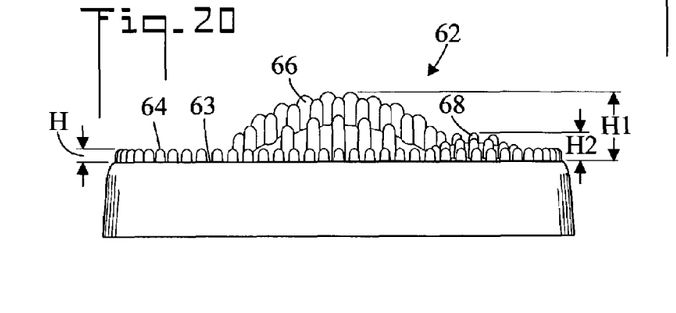
FIG. 20 is an end elevation view of the foot pad.
Figure 22:
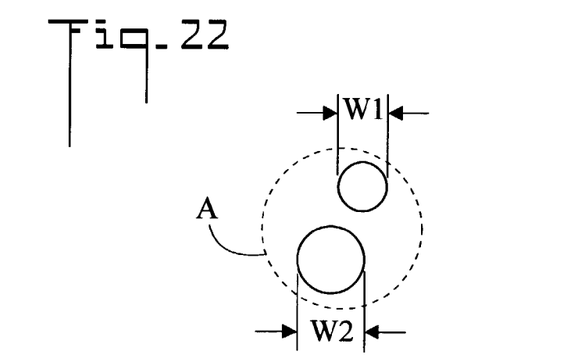
FIG. 22 is an enlarged view of area A of FIG. 18.

FIG. 22 is an enlarged view of area A of FIG. 18. Knobs having small width W1 and larger width W2 are shown. Because of their different widths, the small and large knobs impart a different type of vibration to the foot of the user.

Figure 23:
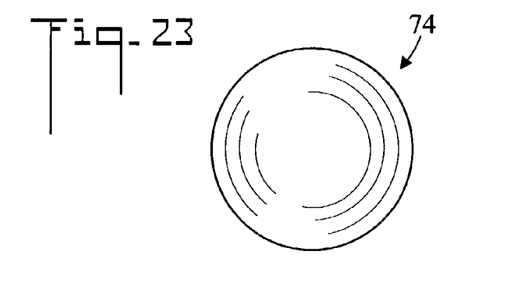
FIG. 23 is an enlarged top plan view of an adapter.
Figure 24:
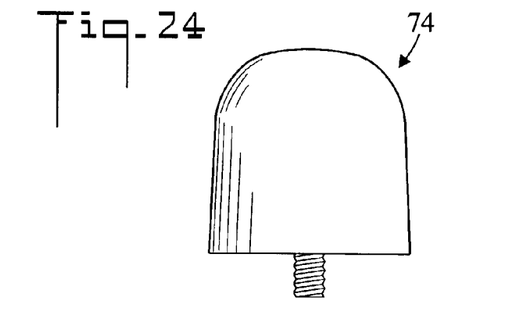
FIG. 24 is an enlarged side elevation view of the adapter.

FIGS. 23–24 are enlarged top plan and side elevation views respectively of a domed adapter 74 which is utilized to attach foot pad 62 to vibrating unit 22. Adapter 74 is attachable to receptacle 26 in vibrating unit 22 in the same fashion as is magnetic massage head 24. And, the domed head of adapter 74 is shaped and dimensioned to snugly fit into cavity 72 in foot pad 62, so that adapter 74 may be attached to receptacle 26 of vibrating unit 22, and then foot pad 62 attached to adapter 74.

Figure 25:
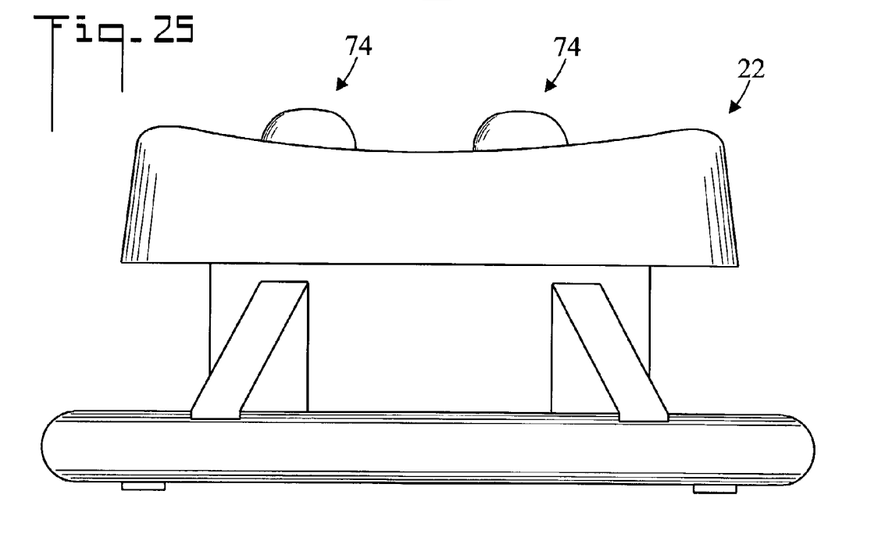
FIG. 25 is a side elevation view of the adapter connected to the vibrating unit.

FIG. 25 shows adapter 74 connected to vibrating unit 22. After adapter 74 is installed, foot pad 62 is attached to adapter 74 as is shown in FIGS. 16 and 17. In the shown embodiment, vibrating unit 22 including four spaced-apart attachment-accepting receptacles 26 to which four adapters 74 are attached. The four cavities 72 of foot pad 62 install over the four adapters 74.

Figure 26:
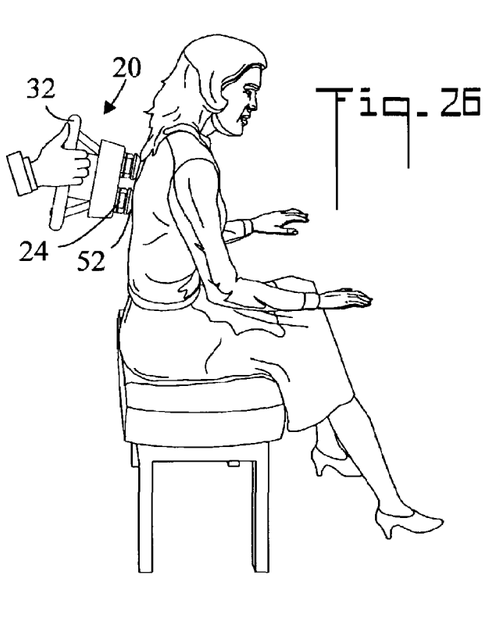
FIG. 26 is a reduced side elevation view of the massage system in use.

FIG. 26 is a reduced side elevation view of massage system 20 in use. Massage pad 52 has been installed on magnetic massage head 24. A second person is holding handle 32 and using massage pad 52 to massage a recipient.

Figure 27:
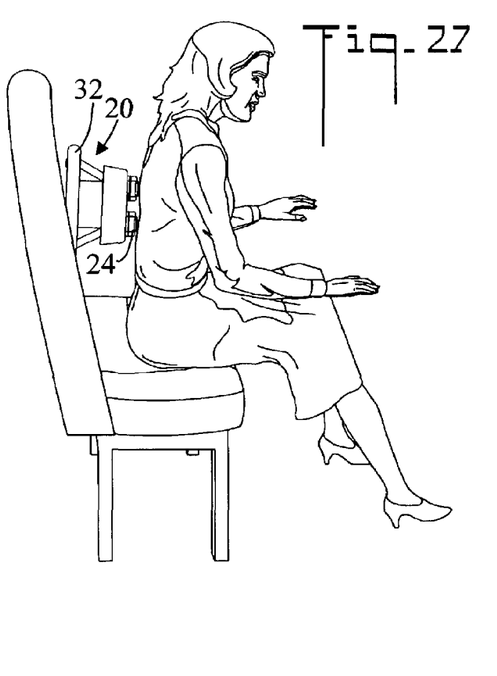
FIG. 27 is a second reduced side elevation view of the massage system in use.

FIG. 27 is a second reduced side elevation view of the massage system 20 in use. In this embodiment of the invention, the user has placed massage system 20 between herself and the back of a chair to effect the massage. A second person is not required. Also, it is noted that in this embodiment magnetic massage head 24 is directly used to effect the massage. Massage pad 52 is not installed.

Figure 28:
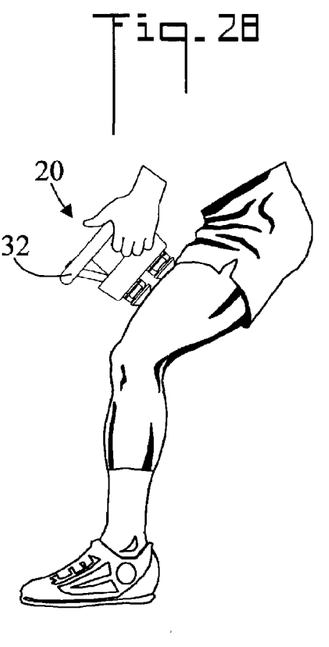
FIG. 28 is a third reduced side elevation view of the massage system in use.

FIG. 28 is a third reduced side elevation view of the massage system 20 in use. In this embodiment the user holds massage system 20 by handle 32 and performs massage without the need of a second person.

Figure 29:
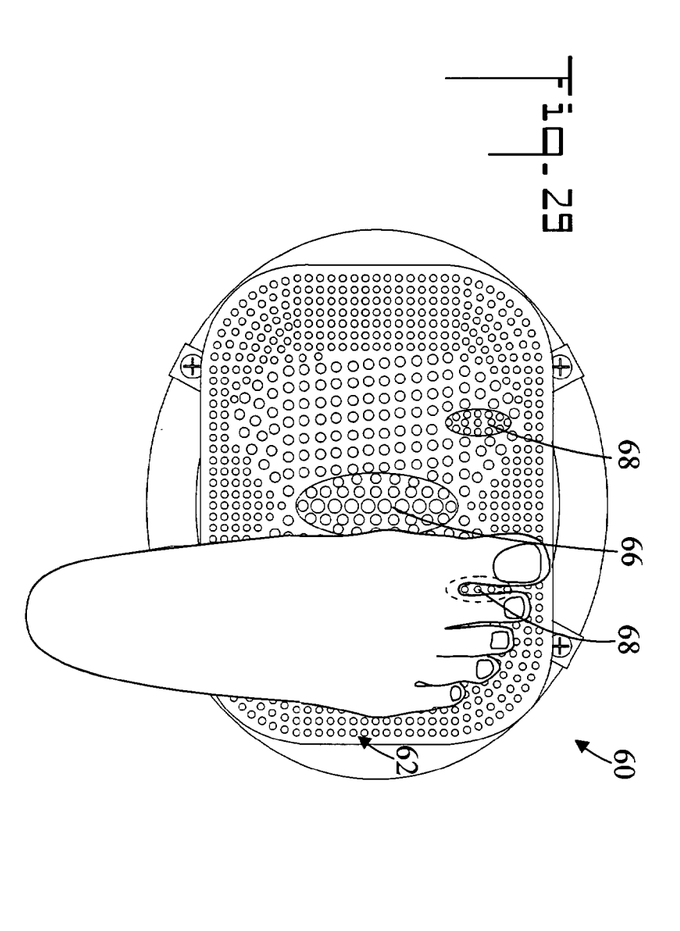
FIG. 29 is a top plan view of the second embodiment of the massage system in use; and, FIG. 30 is a second top plan view of the second embodiment of the massage system being in use.

FIG. 29 is a top plan view of the second embodiment of the massage 60 system in use. The user's foot has been placed on foot pad 62 with the user's toes resting upon raised second knobs 68 to effect toe massage. While in the shown embodiment the user is bare foot, the present invention may also be used when the user is wearing socks or even shoes.

Figure 30:
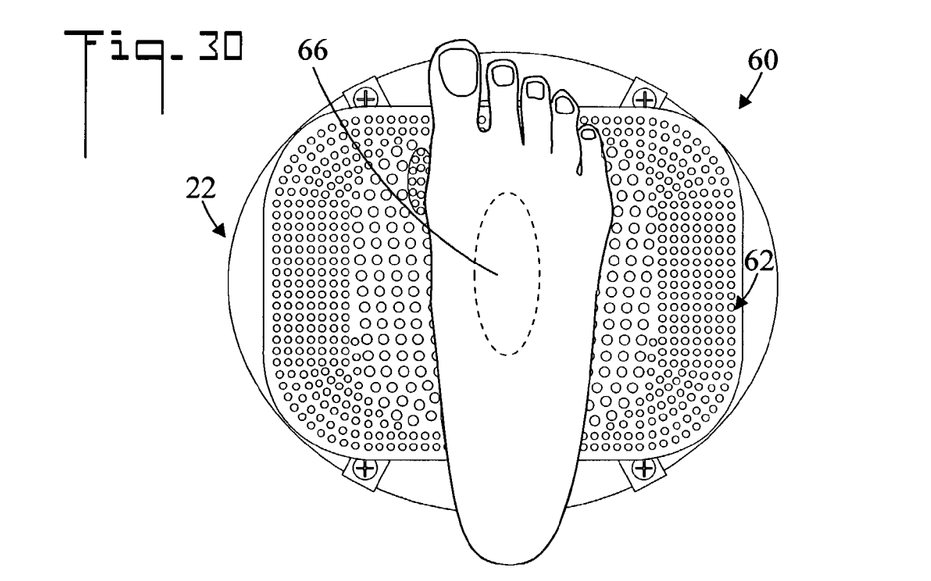

FIG. 30 is a second top plan view of the second embodiment of the massage system 60 in use. The user's foot has been placed on foot pad 62 with the user's arch resting upon raised first knobs 66 to effect arch massage.

The preferred embodiments of the invention described herein are exemplary and numerous modifications, variations, and rearrangements can be readily envisioned to achieve an equivalent result, all of which are intended to be embraced within the scope of the appended claims.

We claim:

1. A massage system, comprising:
   a vibrating unit, said vibrating unit having at least one attachment-accepting receptacle;
   a magnetic massage head attachable to said receptacle, said magnetic massage head including a rotating member which rotates about an axle when said vibrating unit is activated;
   a magnet carried by said rotating member, so that when said vibrating unit is activated, said magnet rotates about said axle thereby creating a rotating magnetic field; and,
   said magnetic massage head having a transparent housing so that said rotation of said rotating member about said axle may be observed.

2. A massage system, comprising:
   a vibrating unit, said vibrating unit having at least one attachment-accepting receptacle;
   a magnetic massage head attachable to said receptacle, said magnetic massage head including a rotating member which rotates about an axle when said vibrating unit is activated;
   a magnet carried by said rotating member, so that when said vibrating unit is activated, said magnet rotates about said axle thereby creating a rotating magnetic field;
   said vibrating unit having a handle;
   said handle covered with a cushioning material; and,
   said handle having a flattened steering wheel shape.

3. A massage system, comprising:
   a vibrating unit, said vibrating unit having at least one attachment-accepting receptacle;
   a magnetic massage head attachable to said receptacle, said magnetic massage head including a rotating member which rotates about an axle when said vibrating unit is activated;
   a magnet carried by said rotating member, so that when said vibrating unit is activated, said magnet rotates about said axle thereby creating a rotating magnetic field; and,
   a massage pad shaped and dimensioned to removably attach to said magnetic massage head, said massage pad having a shape of a truncated pyramid.

4. A massage system, comprising:
   a vibrating unit, said vibrating unit having at least one attachment-accepting receptacle;
   a magnetic massage head attachable to said receptacle, said magnetic massage head including a rotating member which rotates about an axle when said vibrating unit is activated;
   a magnet carried by said rotating member, so that when said vibrating unit is activated, said magnet rotates about said axle thereby creating a rotating magnetic field;
   said rotating member including a disc which is fabricated from a non-magnetic material;
   said magnet disposed within a sector of said disc, so that as said disc rotates about said axle said rotating magnetic field pulsates;
   said magnetic massage head having a transparent housing so that said rotation of said disc about said axle may be observed; and,
   a massage pad shaped and dimensioned to removably attach to said magnetic massage head, said massage pad having a shape of a truncated pyramid.

5. A massage system, comprising:
   a vibrating unit, said vibrating unit having a plurality of attachment-accepting receptacles;
   a plurality of massage heads removably attachable to said plurality of attachment-accepting receptacles;
   a foot pad attachable to said vibrating unit, so that when said vibrating unit is activated, said foot pad vibrates;
   said foot pad including a front surface having a plurality of foot-massaging knobs;
   said plurality of foot-massaging knobs including a group of base knobs having a maximum height H;
   said plurality of foot-massaging knobs including a group of raised first knobs having a maximum height H1 which is greater than said maximum height H of said base knobs;
   said foot pad have a back side opposite from said front surface;
   said back side including a plurality of cavities, one said cavity for each of said plurality of attachment-accepting receptacles;

a plurality of foot pad adapters removably attachable to said plurality of attachment-accepting receptacles, said plurality of foot pad adapters shaped and dimensioned to snugly fit into said plurality of cavities wherein one said foot pad adapter is received by each said cavity; and, so that said plurality of foot pad adapters may be removably attached to said plurality of attachment-accepting receptacles, and said foot pad removably attached to said plurality of foot pad adapters.

6. A massage system according to claim 5, further including:

said vibrating unit including four spaced-apart attachment-accepting receptacles;

four said adapters attachable to said four receptacles; and, said back side including four said cavities.

7. A massage system, comprising:

a vibrating unit, said vibrating unit having at least one attachment-accepting receptacle;

a magnetic massage head attachable to said receptacle, said magnetic massage head including a rotating member which rotates about an axle when said vibrating unit is activated;

a magnet carried by said rotating member, so that when said vibrating unit is activated, said magnet rotates about said axle thereby creating a rotating magnetic field;

a foot pad attachable to said vibrating unit, so that when said vibrating unit is activated, said foot pad vibrates;

said foot pad including a front surface having a plurality of foot-massaging knobs;

said plurality of foot-massaging knobs including a group of base knobs having a maximum height H; and, said plurality of foot-massaging knobs including a group of raised first knobs having a maximum height H1 which is greater than said maximum height H of said base knobs.

8. A massage system according to claim 7, further including:

said rotating member including a disc which is fabricated from a non-magnetic material;

said magnet disposed within a sector of said disc, so that as said disc rotates about said axle said rotating magnetic field pulsates;

said magnetic massage head having a transparent housing so that said rotation of said disc about said axle may be observed;

a massage pad shaped and dimensioned to removably attach to said magnetic massage head, said massage pad having a shape of a truncated pyramid;

said plurality of foot-massaging knobs including knobs of at least two different widths;

said plurality of foot-massaging knobs including a group of raised second knobs having a maximum height H2 which is greater than said maximum height H of said base knobs, but less than said maximum height H1 of said first knobs;

said plurality of foot-massaging knobs including two groups of said second knobs;

all of said base knobs being of substantially the same height; and, said vibrating unit having a handle covered with a cushioning material.

* * * * *